United States Patent [19]

Valenta

[11] 4,134,920
[45] Jan. 16, 1979

[54] 14β-HYDROXYANDROSTANES

[76] Inventor: Zdenek Valenta, 872 Windsor St., Fredericton, New Brunswick, Canada

[21] Appl. No.: 811,393

[22] Filed: Jun. 29, 1977

[51] Int. Cl.$^2$ ............................................. C07C 49/48
[52] U.S. Cl. ........................... 260/586 E; 260/397.45; 260/586 F
[58] Field of Search ...................... 260/397.45, 586 E

[56] References Cited
PUBLICATIONS

Ruppert et al., Chem. Ber., vol. 106, pp. 3636–3644 (1973).

Primary Examiner—Gerald A. Schwartz
Attorney, Agent, or Firm—Jon S. Saxe; George M. Gould; Raymond R. Wittekind

[57] ABSTRACT

14β-Hydroxyandrostanes and processes for the preparation thereof in which the 14β-hydroxy group is fabricated internally by means of a novel cyclization of 8,14-seco-4,6,9(11)-androstatrien-3,14,17-triones is disclosed.

The 14β-hydroxyandrostanes are useful as precursors for the synthesis of cardenolides and related products.

2 Claims, No Drawings

14β-HYDROXYANDROSTANES

BACKGROUND OF THE INVENTION

The cardenolides are a group of cardio-active steroids characterized by the presence of a 14β-hydroxyl function and a 17β-butenolide moiety ("Steroids", L. F. Fieser and M. Fieser, Reinhold Publishing Corporation, New York, New York, 1959, ch. 20). Many of these compounds, which occur in small amounts in various plants, are potent cardiac stimulants (G. K. Moe and A. E. Farah, in "The Pharmacological Bases of Therapeutics", 4th Ed., L. S. Goodman and A. Gilman, ed., The Macmillan Company, New York, N.Y., 1970, ch. 31), and for this reason, considerable synthetic effort directed toward their synthesis has been expended in the past. Prior to 1962, the fruits of these labors have been minimal. While methods for the introduction of the 14β-hydroxy group and the construction of the 17β-butenolide have been developed utilizing model compounds, they have been uniformly inapplicable in the natural series. In 1962, the problems associated with the configurational instability of the 17β-butenolide and the lability of the 14β-hydroxy function during construction of the butenolide were resolved in the first reported synthesis of a cardenolide, digitoxigenin. This synthesis, while recognized as a scientific breakthrough, suffers from the disadvantage of starting from difficultly available materials resulting in low overall yields (R. Deghenghi, Pure and Appl. Chem. 21, 153 [1970]). Since 1962, improved synthesis of cardenolides have been reported. These syntheses, like the original synthesis of digitoxigenin, however, start with preformed steroids, involve the direct introduction of the 14β-hydroxyl group and suffer from the predominant disadvantage of the unavailability of the precursor steroids. Thus, an efficient synthesis of 14β-hydroxysteroidyl cardenolide precursors, making ultimate cardenolides readily available for therapeutic use, would be a major advance in this area (P. J. Sykes and S. J. Whitehurst, in "Terpenoids and Steroids", K. H. Overton, ed., Volume 5, The Chemical Society, London, England, 1975, page 354).

DETAILED DESCRIPTION OF THE INVENTION

The present invention relates to novel 14β-hydroxyandrostanes and novel, efficient processes for the preparation thereof. More particularly, the present invention relates to 14β-hydroxy-4,6,9(11)-androstatrienes, 14β-hydroxy-4,9(11)-androstadienes and 14β-hydroxy-9(11)-androstenes and processes for the preparation thereof involving the steps of converting a 1-hydroxy-8a-lower alkyl-1-vinyl-1,2,3,4,6,7,8,8a-octahydro-6-naphthalenone to a 1-(2-chloroethylidene)-8a-lower alkyl-1,2,3,4,6,7,8,8a-octahydro-6-naphthalenone, condensing the 1-(2-chloroethylidene)-8a-lower alkyl-1,2,3,4,6,7,8,8a-octahydro-6-naphthalenone with a 2-lower alkyl-1,3-cyclopentandione to form a 8,14-seco-4,9(11)-androstadiene-3,14,17-trione, dehydrogenating the 8,14-seco-4,9(11)-androstadiene-3,14,17-trione to 8,14-seco-4,6,9(11)-androstatriene-3,14,17-trione, cyclizing the 8,14-seco-4,6,9(11)-androstatriene-3,14,17-trione to a 14β-hydroxy-4,6,9(11)-androstatriene-3,17-dione, hydrogenating the 14β-hydroxy-4,6,9(11)-androstatriene-3,17-dione to a 14β-hydroxy-4,9(11)-androstadiene-3,17-dione and chemically reducing and then oxidizing the 14β-hydroxy-4,9(11)-androstadiene-3,17-dione to a 14β-hydroxy-9(11)-androstene-3,17-dione.

The present invention, also more particularly, relates to an alternative process for the preparation of 8,14-seco-4,6,9(11)-androstatriene-3,14,17-trione involving the steps of dehydrogenating 1-hydroxy-8a-lower alkyl-1-vinyl-1,2,3,4,6,7,8,8a-octahydro-6-naphthalenone to a 1-hydroxy-8a-methyl-1-vinyl-1,2,6,7,8,8a-hexahydro-6-naphthalenone, converting the 1-hydroxy-8a-methyl-1-vinyl-1,2,6,7,8,8a-hexahydro-6-naphthalenone to a 1-(2-haloethylidene)-8a-methyl-1,2,6,7,8,8a-hexahydro-6-naphthalenone and condensing the 1-(2-haloethylidene)-8a-methyl-1,2,6,7,8,8a-hexahydro-6-naphthalenone with a 2-lower alkyl-1,3-cyclopentadione to form the 8,14-seco-4,6,9(11)-androstatriene-3,14,17-trione.

As used throughout the specification and appended claims, the term "alkane" refers to a straight or branched chain hydrocarbon such as methane, ethane, 2-butane, hexane, 2-octane and so forth. The term "alkyl" refers to a radical derived by abstraction of a hydrogen atom from an alkane. Examples of "alkyl" radicals are methyl, ethyl, tert.-butyl, hexyl, 2-octyl and so forth. The term "alkanol" refers to an alcohol derived by replacement of a hydrogen atom of an alkane by a hydroxy radical. Examples of alkanols are methanol, ethanol, 2-butanol, hexanol, 2-octanol and so forth. The term "alkoxide" refers to the anion derived by abstraction of a proton from the hydroxyl group of an alkanol. Examples of alkoxides are methoxide, ethoxide, 2-butoxide, hexoxide, 2-octoxide and so forth. The term "alkanoic acid" refers to a carboxylic acid derived by replacement of a hydrogen atom of an alkane by a carboxylic acid group. Examples of alkanoic acids are acetic acid, 2,2-dimethylacetic acid, hexanoic acid, octanoic acid and so forth. The term "lower" refers to the numerical range of 1 to 8.

In the formulas presented herein, the relative stereochemistry of the various substituents on the cyclic nucleus is indicated by one of three notations: a solid line (—), indicating the substituent is in the β-orientation, i.e., above the plane of the molecule; a dotted line (--), indicating the substituent is in the α-orientation, i.e., below the plane of the molecule; or a wavy line (∿), indicating the substituent may be either in the α- or β-configuration or may be a mixture of both.

For convenience, the stereochemistry of the substituent $R_1$ at the C-10 position (steroid numbering) has been arbitrarily indicated as the β-orientation; thus all the compounds are depicted as having the natural absolute configuration. It should be understood that the invention described herein is equally applicable to compounds having either the natural or the unnatural configuration, for example, to racemic mixtures.

If it is desired to prepare optically active steroids, one may either begin with a known optically active compound of formula 1

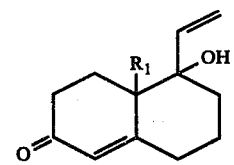

wherein $R_1$ is lower alkyl or alternatively, one may start with a racemic compound of formula I and may carry out an optical resolution at one of the intermediate stages, or at the final product by methods known per se.
The processes of the present invention for the preparation of 14β-hydroxyandrostanes are illustrated in the Reaction Scheme.
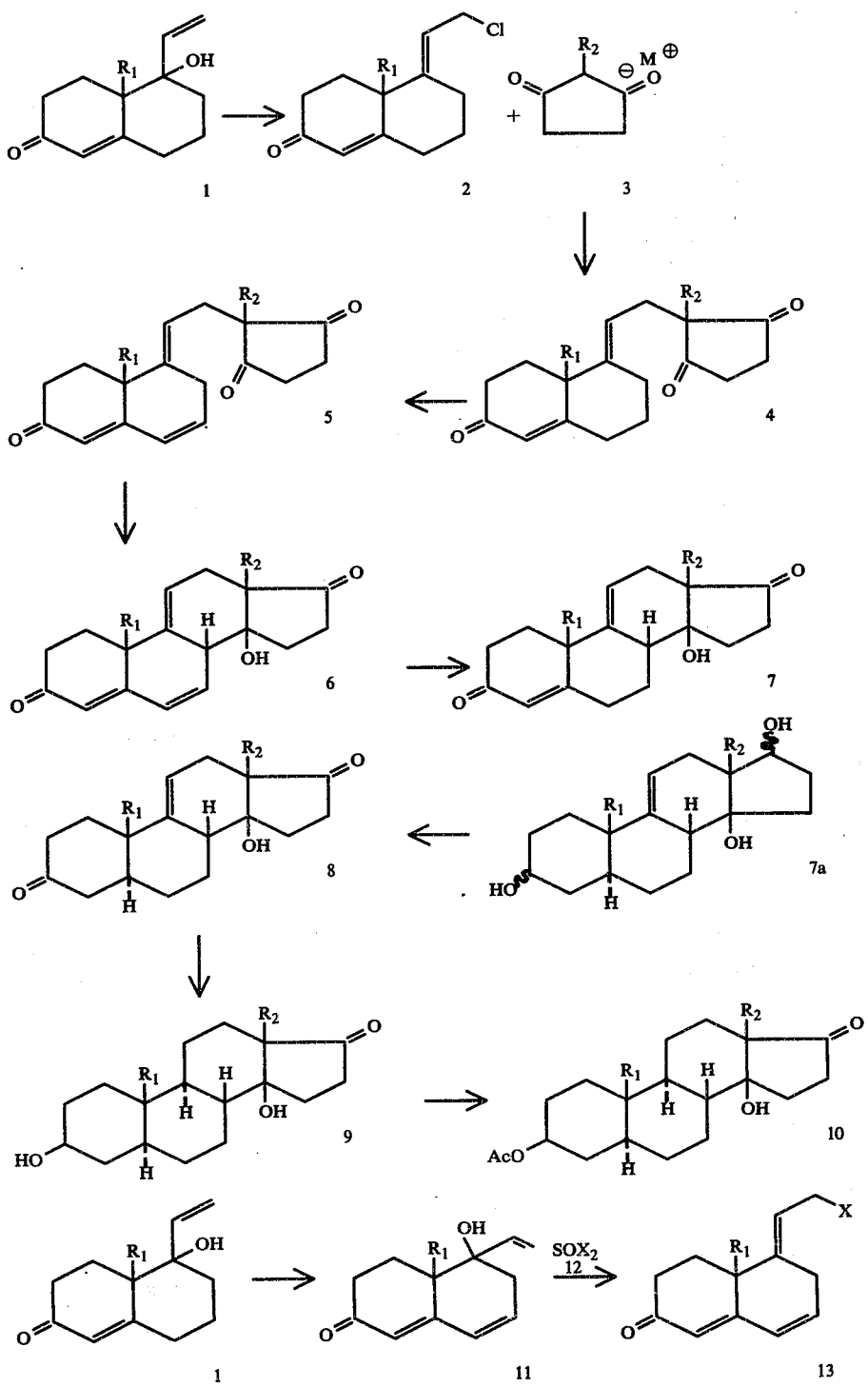
Reaction Scheme -continued
Reaction Scheme

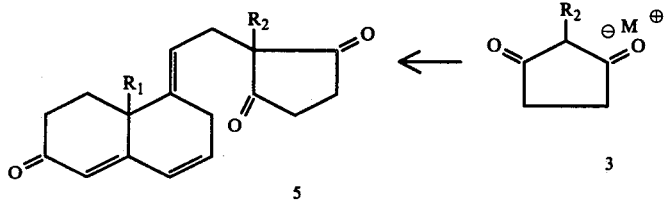

wherein $R_1$ and $R_2$ are each independently lower alkyl; X is chloro or bromo, and $M^{\oplus}$ is an alkali metal.

In the first step of the instant process, a 1-hydroxy-8a-lower alkyl-octahydro-6-naphthalenone of formula 1, the preparation of which is described by S. Swaminathan et al., Tetrahedron Letters, 729 (1962), is treated with thionyl chloride to give a 1-(2-chloroethylidene)-8a-lower alkyl-1,2,3,4,6,7,8,8a-octahydro-6-naphthalenone of formula 2. The displacement-rearrangement reaction is generally conducted by dissolving the vinyl carbinol in a halocarbon, such as methylene chloride, chloroform, 1,2-dichloroethane, 1,1-dichloroethane and the like, at a reduced temperature of about 0° C. to about −70° C. and then adding a solution of a polar aprotic solvent, such as N,N-dimethylacetamide, N,N-dimethylformamide, hexamethylphosphoramide and the like, in a halocarbon, such as methylene chloride, chloroform, 1,2-dichloroethane, 1,1-dichloroethane and the like, also at a temperature of about 0° C. to about −70° C. The reaction is preferably carried out in methylene chloride using N,N-dimethylformamide as the polar aprotic solvent at a temperature of about −60° C.

The preparation of 1-(2-bromoethylidene)-8a-methyl-1,2,3,4,6,7,8,8a-octahydro-6-naphthalenone has been reported by J. Ruppert et al. in Chem. Ber., 106, 3636 (1973).

In the second step, the allylic chloride of formula 2 is condensed with an alkali metal salt, such as the lithium, sodium or potassium salt, of a 2-lower alkylcyclopentandione-1,3 of formula 3 to afford a seco-androstadiene of formula 4. The condensation is suitably performed in the presence of an alkali metal iodide, such as lithium, sodium or potassium iodide, by treating a solution of the chloride of formula 2 and the alkali metal iodide dissolved in a polar aprotic solvent such as N,N-dimethylbutamide, N,N-dimethylformamide, hexamethylphosphoramide and the like, with a solution of the alkali metal salt of the dione of formula 3 dissolved in a lower alkanol, such as methanol, ethanol, 2-propanol and the like. The condensation is preferably carried out in N,N-dimethylformamide using sodium iodide and the sodium salt of the dione of formula 3 dissolved in methanol.

The alkali metal salt of the 2-lower alkylcyclopentandione-1,3 of formula 3 may be conveniently prepared by treating the dione of formula 3 with an alkali metal lower alkoxide, such as lithium methoxide, sodium methoxide, sodium ethoxide, potassium 2-butoxide and the like, in a lower alkanol, such as methanol, ethanol, 2-butanol and the like. It is preferable to employ the lower alkanol from which the alkoxide is derived. It is most preferable to employ sodium methoxide in methanol.

Optically active 8,14-seco-4,9(11)-androstadiene-3,14,17-trione, the compound of formula 4 wherein $R_1$ and $R_2$ are methyl, has been prepared by J. Ruppert et al. (Chem. Ber., 106, 3636 [1973]) by a related process in an inferior yield.

In the third step of the present process, the 6,7-double bond (steroid numbering) is introduced by dehydrogenation of an 8,14-seco-androstadiene of formula 4. This step is generally accomplished by treatment of the 8,14-seco-androstadiene with a p-quinone, such as 1,4-benzoquinone, 1,4-naphthaquinone, 2,3,5,6-tetrachloro-1,4-benzoquinone, 2,3-dichloro-5,6-dicyano-1,4-benzoquinone, 2,3-dibromo-5,6-dicyano-1,4-benzoquinone and the like, in an inert organic solvent, for example, an ethereal solvent, such as tetrahydrofuran, dioxane, 1,2-dimethoxyethane, bis-(2-methoxyethyl)ether and the like. 2,3-Dichloro-5,6-dicyano-1,4-benzoquinone is the preferred dehydrogenation agent. Dioxane is the preferred reaction solvent.

To promote the dehydrogenation, i.e. the conversion of a seco-steroid of formula 4 to a seco-steroid of formula 5, a catalytic amount of a strong mineral acid, such as hydrogen chloride, hydrogen bromide and the like, or a sulfonic acid, such as methanesulfonic acid, benzenesulfonic acid, p-toluenesulfonic acid and the like, may be added to the reaction mixture. About 0.2% by weight of hydrogen chloride in the inert organic solvent is the preferred promoter.

Alternatively, the 8,14-seco-androstatriene of formula 5 may be prepared by a comparable series of reactions in which the 6,7-double bond of the ultimate seco-steroid is constructed in the initial step of the process and carried through to the final product. In the first step of the alternative process, a 1-hydroxy-8a-lower alkyl-1-vinyl-1,2,3,4,6,7,8,8a-octahydro-6-naphthalenone of formula 1 is dehydrogenated to a 1-hydroxy-8a-lower alkyl-1-vinyl-1,2,6,7,8,8a-hexahydro-6-naphthalenone of formula 11. The dehydrogenation is performed employing a p-quinone in an inert organic solvent. Suitable p-quinones include 1,4-benzoquinone, 1,4-naphthaquinone, 2,3,5,6-tetrachloro-1,4-benzoquinone, 2,3-dichloro-5,6-dicyano-1,4-benzoquinone, 2,3-dibromo-5,6-dicyano-1,4-benzoquinone and the like. Suitable inert organic solvents include, for example, ethereal solvents, such as tetrahydrofuran, dioxane, 1,2-dimethoxyethane, bis-(2-methoxyethyl)ether and the like. A strong mineral acid, such as hydrogen chloride, hydrogen bromide and the like, or a sulfonic acid, such as methanesulfonic acid, benzenesulfonic acid, p-toluenesulfonic acid and the like, may be utilized in catalytic amounts to promote the dehydrogenation. The reaction is preferably conducted in dioxane containing about 0.4% by weight of hydrogen chloride using 2,3-dichloro-5,6-dicyano-1,4-benzoquinone as the dehydrogenating agent.

The hexahydro-6-naphthalenone of formula 11, so-obtained, is then substitutively-rearranged by means of a thionyl halide of formula 12 in an inert organic solvent, for example, a halocarbon, such as methylene chloride, chloroform, 1,1-dichloroethane, 1,2-dichloroethane and the like. Thionyl chloride dissolved in methylene chloride is the preferred reaction system.

An organic base, such as triethyl amine, pyridine, s-collidine and the like may be employed in the substitution-rearrangement to scavenge formed hydrogen halide. Pyridine is the preferred scavenger.

While the temperature at which the substitution-rearrangement is performed is not narrowly critical, it is preferred to conduct the reaction at a reduced temperature within the range of about −40° to about 20° C., a temperature of about 0° C. being particularly preferred.

To complete the alternative synthesis of the seco-androstatriene of formula 5, the allylic halide of formula 13 is condensed with an alkali metal salt, for example, the lithium, sodium or potassium salt, of a 2-lower alkylcyclopentandione-1,3 of formula 3 to afford the seco-steroid of formula 5. Like the condensation of the allylic chloride of formula 2 with the alkali metal salt of a 2-lower alkylcyclopentandione-1,3 of formula 3 to furnish the seco-steroid of formula 4, the instant condensation is suitably conducted in the presence of an alkali metal iodide, such as lithium, sodium or potassium iodide, by treating a solution of the halide of formula 13 and the alkali metal iodide dissolved in a polar aprotic solvent, such as N,N-dimethylacetamide, N,N-dimethylformamide, hexamethylphosphoramide and the like, with a solution of the alkali metal salt of the dione of formula 3 dissolved in a lower alkanol, such as methanol, ethanol, 2-propanol and the like. This condensation, also like that performed with the allylic chloride of formula 2, is preferably carried out in N,N-dimethylformamide using sodium iodide and the sodium salt of the dione of formula 3 dissolved in methanol.

In the next step of the primary process of the present invention, the seco-androstatriene of formula 5 is cyclized to the 14β-hydroxy-4,6,9(11)-androstatriene-3,17-dione of formula 6 under basic conditions. The cyclization is generally performed by dissolving the seco-steroid of formula 5 in a suitable solvent, for example, a lower alkanol, such as methanol, ethanol, 2-butanol and the like and then adjusting the pH to a value within the range of 7.5–12 units by adding a base, for example, an alkali metal alkoxide, such as lithium methoxide, sodium methoxide, sodium ethoxide, potassium butoxide and the like. The cyclization is preferably conducted in methanol containing sufficient sodium methoxide to attain a reaction pH within the range of 8.0–9.5 units.

The 6,7-double bond of the 14β-hydroxyandrostatriene of formula 6 is then hydrogenated to the 14β-hydroxyandrostadiene of formula 7. The hydrogenation is conveniently conducted at a pressure of from about 1 atmosphere to about 5 atmospheres of hydrogen and a temperature within the range of about 20° to about 50° C. in the presence of a metal hydrogenation catalyst, such as, for example, platinum, palladium, rhodium, ruthenium and the like, in a suitable inert solvent. Suitable inert solvents include aromatic hydrocarbons, such as benzene, toluene, xylene and the like, and alkanols, such as methanol, ethanol, 2-butanol and the like. The hydrogenation is preferably conducted at a pressure of about 1 atmosphere of hydrogen and at a temperature of about 25° C. using a palladium catalyst suspended in a solvent comprising benzene and ethanol. A particularly preferred hydrogenation catalyst is 2% palladium-on-strontium carbonate.

An isomeric 14-hydroxy-4,9(11)-androstadien-3,17-dione was recently disclosed by J. Ruppert et al. in Chem. Ber., 106, 3636 (1973). The reported isomer of 14β-hydroxy-4,9(11)-androstadien-3,17-dione of the present invention is most probably either the 8- or 13,14-epimer of the androstadiene of the present invention and therefore not useful for the preparation of natural cardenolides.

In the next step of the instant process for the preparation of 14β-hydroxyandrostanes, the 14β-hydroxyandrostadien-3,17-dione of formula 7 is reduced to the 14β-hydroxyandrosten-3,17-diol of formula 7a, the 3- and 17-hydroxy groups of which are then oxidized to afford a 14β-hydroxyandrosten-3,17-dione of formula 8. The reduction aspect of this step may be accomplished by means of an alkali metal, for example, lithium, sodium or potassium, or an alkaline earth metal, for example, calcium, dissolved in liquid ammonia or a liquid amine. Alkali metals are preferred, lithium being most preferred. Suitable liquid amines include methylamine, ethylamine, propylamine, L-propylamine, butylamine and ethylenediamine. Of the liquid amines, ethylamine and ethylenediamine are preferred, liquid ammonia being particularly preferred as the ammonical component.

To solubilize the organic substrate, a cosolvent, for example, an ethereal solvent, such as diethyl ether, 1,2-dimethoxyethane, tetrahydrofuran, dioxane and the like, may be employed. Dioxane and tetrahydrofuran are the preferred cosolvents, dioxane being particularly preferred.

To promote the dissolving metal reduction, a proton source is generally employed. Suitable proton sources include lower alkanols, such as methanol, ethanol, 2-propanol, tert.-butanol and the like. Ethanol and tert.-butanol are preferred. tert.-Butanol is most preferred.

The reduction is usually conducted at the boiling point of the ammonical component when its boiling point is below room temperature. When the boiling point of the ammonical component is above room temperature, the reaction is generally performed at room temperature, although when ethylenediamine is employed, reaction temperature above room temperature can be utilized, for example, from slightly above room temperature to near the reflux temperature of the diamine.

The oxidation aspect of this step, i.e., the conversion of the 14β-hydroxyandrosten-3,17-diol of formula 7a to the 14β-hydroxyandrosten-3,17-dione of formula 8, is accomplished by means of non-acidic oxidizing systems in inert solvents. Suitable non-acidic oxidizing systems include chromic acid-pyridine, pyridinium chlorochromate and the like. Suitable inert solvents include, for example, halocarbons, such as methylene chloride, chloroform, 1,1-dichloroethane, 1,2-dichloroethane and the like. In the preferred embodiment, the 14β-hydroxyandrostane of formula 7a is oxidized with pyridinium chlorochromate in methylene chloride.

In the last step of the present process, the 9(11)-double bond of a 14β-hydroxyandrosten-3,17-dione is saturated with hydrogen with concomitant reduction of the 3-keto group to a hydroxy function to give a 3,14β-hydroxy-androstan-17-one of formula 9. The reduction is suitably effected at a hydrogen pressure of from about one atmosphere to about 5 atmospheres and a temperature within the range of about 20° to about 50° C. in the presence of a metal hydrogenation catalyst, such as, for example, platinum, palladium, rhodium, ruthenium and the like, in an inert solvent. Suitable inert solvents include, for example, lower alkanoic acids, such as acetic acid, propionic acid and the like. The reduction is preferably conducted at a pressure of about one atmosphere of hydrogen and a temperature of about 25° C. using platinum oxide suspended in glacial acetic acid.

3β,14β-Dihydroxyandrostan-17-one may be converted to the 3-acetyl derivative of formula 10 by standard methods well known in the art involving reaction with, for example, acetic anhydride in the presence of a base, such as pyridine. 3β-Acetoxy-14β-hydroxyandrostan-17-one has been converted to the cardenolide, uzarigenin, which exhibits not only cardiac stimulant activity, but is also useful for the treatment of diarrhea and bacillary dysentery (U.S. Pat. No. 3,595,883, issued July 27, 1971).

The following examples are illustrative only of the invention and are not to be construed as limitative thereof in any manner. All temperatures are reported in degrees Centigrade.

EXAMPLE 1

Preparation of 1-(2-chloroethylidene)-8a-methyl-1,2,3,4,6,7,8,8a-octahydro-6-naphthalenone 1-Hydroxy-8a-methyl-1-vinyl-1,2,3,4,6,7,8,8a-octahydro-6-naphthalenone (17.0 g.) dissolved in 60 ml. of methylene chloride was cooled in a dry ice-acetone bath to −60°, and 13.5 g. of thionyl chloride was added dropwise at this temperature. Then 13.5 ml. of dimethylformamide in 10 ml. of methylene chloride was added at −60° to −40° for about two hours. When starting material could not be detected by thin-layer chromatography in the reaction mixture, water was added and the mixture was washed with an aqueous solution of potassium bicarbonate and then with brine. After drying, the solvent was evaporated under reduced pressure and the crude product containing some dimethylformamide was dissolved in ether and passed through a short column (2 cm.) of alumina to remove polar impurities.

Yield of chloride was about 95%. N.M.R. (CDCl$_3$): δ 1.42 (s, 3H, CH$_3$), 4.12 (d, J = 7.7 Hz, 2H, CH$_2$Cl), 5.53 (d, J = 7.7 Hz, 1H, C=CH), 5.77 (s, 1H, —CO—CH=C).

EXAMPLE 2

Preparation of 8,14-seco-4,9(11)-androstadien-3,14,17-trione

Sodium iodide (12 g.) was dissolved in 150 ml. of dimethylformamide and a solution of 1-(2-chloroethylidene)-8a-methyl-1,2,3,4,6,7,8,8a-octahydro-6-naphthalenone in 30 ml. of dimethylformamide was added. The mixture was stirred at room temperature for 30 minutes and then the sodium salt of 2-methylcyclopentadione-1,3 in 150 ml. of methanol was added. Alkylation was complete in 2 hours at room temperature. Methanol was then evaporated, 1 liter of dry ether was added to the residue and the inorganic precipitate was filtered off and washed with ether. The filtrate was evaporated to dryness under reduced pressure and the residue was passed through a short column of alumina using methylene chloride as a solvent. After evaporation of solvent, the residue was crystallized from ether to give 14 g. of the seco-androstadiene, m.p. 79°–81°. The filtrate was chromatographed on silica to give an additional 3 g. of product.

The overall yield of seco-androstadiene based on 1-hydroxy-8a-methyl-1-vinyl-1,2,3,4,6,7,8,8a-octahydro-6-naphthalenone was 68.7%.

N.M.R. (CDCl$_3$): δ 1.10 (s, 3H, CH$_3$), 1.32 (s, 3H, CH$_3$), 2.7 (s, 4H, OCCH$_2$CH$_2$CO), 5.12 (t, J = 7.8 Hz, 1H, C-11), 5.73 (s, 1H, C-4).

EXAMPLE 3

Preparation of 8,14-seco-4,6,9(11)-androstatrien-3,14,17-trione

To a solution of 8,14-seco-4,9(11)-androstadien-3,14,17-trione (1 g.) in 100 ml. of anhydrous dioxane was added 30 ml. of a solution of hydrogen chloride (1% by weight) in anhydrous dioxane. This mixture was stirred at room temperature for 10 minutes and 2,3-dichloro-5,6-dicyano-1,4-benzoquinone (0.750 g.) in 25 ml. dioxane was added dropwise during 1 hour. After an additional hour, the mixture became light yellow. The precipitate was collected, the filtrate was neutralized with a saturated aqueous solution of potassium bicarbonate and after drying with sodium sulfate, the solvent was evaporated. The residue was dissolved in benzene (50 ml.) and hexane (10 ml.), stirred with a small amount of charcoal, filtered and the charcoal was washed with benzene. Evaporation of solvent gave the seco-androstatriene (0.950 g.) in 70–80% purity (N.M.R.).

N.M.R. (CDCl$_3$): δ 1.14 (s, 3H, CH$_3$ at C-18), 1.27 (s, 3H, CH$_3$ at C-19), 2.69 (s, 4H, O=CCH$_2$CH$_2$C=O), 3.1 (m, 2H at C-8), 5.16 (t, J = 7.8 Hz, 1H at C-11), 5.74 (s, 1H at C-4), 6.4 (s, 2H at C-6 and C-7). U.V.: λ$_{max}$ 284 nm.

EXAMPLE 4

Preparation of 14β-hydroxy-4,6,9(11)-androstatrien-3,17-dione

To a solution of 8,14-seco-4,6,9(11)-androstatrien-3,14,17-trione (0.950 g., 70%–80% pure) in anhydrous methanol (50 ml.) was added an amount of sodium methoxide sufficient to obtain the pH range of 8–9.5. After approximately 2 hours, when the production of 14β-hydroxy-4,6,9(11)-androstatrien-3,17-dione ceased, as determined by thin-layer chromatography, the mixture was neutralized with acetic acid, the methanol was evaporated, and the residue was chromatographed on silica using chloroform and 5% acetone as eluent to afford 0.3 g. of the androstatriene, m.p. 219°–225° (dec.), in 30% yield based on 8,14-seco-4,9(11)-androstadien-3,14,17-trione.

I.R. (CHCl$_3$): 3600 (OH), 3440 (OH), 1745 (C=O), 1660 (C=C-C=O), 1625, 1585 (C=C) cm$^{-1}$; U.V.: 282.5 nm, ε = 18,500; N.M.R. (CDCl$_3$): δ 1.14 (s, 3H, CH$_3$), 1.36 (s, 3H, CH$_3$), 3.25 (m, 1H at C-8), 5.52 (m, 1H at C-11), 5.8 (s, 1H at C-4), 6.46 (m, 2H at C-6 and C-7). M.S.: m/e 298.

EXAMPLE 5

Preparation of 14β-hydroxy-4,9(11)-androstadien-3,17-dione

14β-Hydroxy-4,6,9(11)-androstatrien-3,17-dione (0.200 g.), dissolved in 50 ml. of benzene and 10 ml. of ethanol, was hydrogenated over 0.100 g. of 2% palladium-on-strontium carbonate. After 15 ml. of hydrogen had been consumed, the catalyst was filtered, the solvents evaporated and the residue recrystallized from ether to give 0.170 g. (85%) of the androstadiene, m.p. 170°–172°.

I.R. (CHCl$_3$): 3600 (OH), 3460 (OH), 1740 (C=O), 1660 (C=C-C=O), 1620 cm$^{-1}$ (C=C); N.M.R.

(CDCl$_3$): δ 1.07 (s, 3H, CH$_3$), 1.42 (s, 3H, CH$_3$), 5.55 (m, 1H, at C-11), 5.80 (s, 1H at C-4); (in pyridine D$_5$) 1.25 (s, 3H, CH$_3$), 1.33 (s, 3H, CH$_3$), 5.40 (m, 1H at C-11), 5.90 (s, 1H at C-4), 6.07 (s, 1H, OH).

EXAMPLE 6

Preparation of 14β-hydroxy-9(11)-androsten-3,17-dione

To a solution of 14β-hydroxy-4,9(11)-androstadien-3,17-dione (0.200 g.) in 10 ml. of dioxane, 3 ml. of tert. butanol and 150 ml. of liquid ammonia was added 0.100 g. of lithium and the mixture was stirred at −35° for 10 minutes. The reaction mixture was then treated with an aqueous solution of ammonium chloride and, after evaporation of ammonia, the mixture was extracted with chloroform. The chloroform layer was washed with brine and dried with sodium sulfate. Evaporation of the chloroform afforded 14β-hydroxy-9(11)-androsten-3,17-diol which without purification was oxidized in methylene chloride (50 ml.) with pyridinium chlorochromate (0.300 g.) to the androsten-3,17-dione, which was isolated from the reaction mixture by passing it through a short silica gel column; yield 0.120 g., m.p. 207°–210°.

N.M.R. (CDCl$_3$): δ 1.03 (s, 3H, CH$_3$), 1.22 (s, 3H, CH$_3$), 5.37 (m, 1H at C-11); I.R.: 3600, 3460 (OH), 1745, 1715 cm$^{-1}$.

EXAMPLE 7

Preparation of 3β,14β-dihydroxyandrostan-17-one

The hydrogenation of 14β-hydroxy-9(11)-androsten-3,17-dione (100 mg.) was carried out over 50 mg. of platinum oxide in 25 ml. of glacial acetic acid. When consumption of hydrogen had ceased, the catalyst was filtered, the solvent was evaporated under vacuum and the product was isolated by chromatography on silica gel using a mixture of 10% acetone in chloroform to afford 70 mg. (~70%) of the androstan-17-one, m.p. 214°–217°.

I.R. (CHCL$_3$): 3600, 3460, 1740 cm$^{-1}$; N.M.R. (in CD$_3$OD): δ 0.85 (s, 3H, CH$_3$), 1.01 (s, 3H, CH$_3$), 3.54 (m, 1H at C-3).

EXAMPLE 8

Preparation of 3β-acetoxy-14β-hydroxyandrostan-17-one

3β,14β-Dihydroxyandrostan-17-one (70 mg.) was dissolved in 5 ml. of pyridine and treated with 1 ml. of acetic anhydride at room temperature for 15 hours. After evaporation of solvents, the residue was crystallized from ether to give 70 mg. of the acetate, m.p. 182°–184°.

N.M.R. (CDCl$_3$): δ 0.84 (s, 3H, CH$_3$), 1.05 (s, 3H, CH$_3$), 2.03 (s, 3H, CH$_3$CO), 4.70 (m, 1H at C-3).

EXAMPLE 9

Preparation of 1-hydroxy-8a-methyl-1-vinyl-1,2,6,7,8,8a-hexahydro-6-naphthalenone To a solution of 2.2 g. of 1-hydroxy-8a-methyl-1-vinyl-1,2,3,4,6,7,8,8a-octahydro-6-naphthalenone in anhydrous dioxane (220 ml.) was added anhydrous dioxane (40 ml.) containing 2.6% by weight of hydrogen chloride. After stirring at room temperature for 10 minutes, 2,3-dichloro-5,6-dicyano-1,4-benzoquinone (2.497 g.) was added in one portion and stirring was continued at room temperature for 8 hours. The initially dark brown solution faded to a very light yellow color with precipitation of 2,3-dichloro-5,6-dicyano-1,4-hydroquinone. The precipitate was collected and washed twice with methylene chloride. The filtrate was neutralized with a saturated sodium bicarbonate solution and dried over sodium sulfate. Evaporation of solvent followed by chromatography using ethyl acetate-hexane (3:1) gave 1.5 g. (72%) of the hexahydro-6-naphthalenone, m.p. 101°–102°.

N.M.R. (CDCl$_3$): δ 1.30 (s, 3H, CH$_3$), 5.0–6.3 (m, 6H, olefinic protons); I.R. (CHCl$_3$): 1660, 1620 cm$^{-1}$; U.V.: λ$_{max}$ 285 nm.

EXAMPLE 10

Preparation of 1-(2-chloroethylidene)-8a-methyl-1,2,6,7,8,8a-hexahydro-6-naphthalenone To a solution of 1-hydroxy-8a-methyl-1-vinyl-1,2,6,7,8,8a-hexahydro-6-naphthalenone (0.204 g.) in anhydrous methylene chloride (20 ml.) was added 0.5 ml. of pyridine. The reaction mixture was cooled in an ice-bath and thionyl chloride (150 mg.) was added. After 5 minutes, the reaction mixture was diluted with methylene chloride (20 ml.) and water (10 ml.) and neutralized with saturated sodium bicarbonate solution (5 ml.). The aqueous layer was extracted with methylene chloride (3 × 25 ml.) and the combined organic layers were washed with brine and dried over sodium sulfate. Evaporation of solvent gave 217 mg. of the oily chloride.

N.M.R. (CDCl$_3$): δ 1.35 (s, 3H, CH$_3$), 4.14 (d, 2H, J = 8 Hz, —CH$_2$Cl), 3.16 (m, 2H, CH$_2$), 5.66 (t, 1H, C=CH-CH$_2$Cl), 5.76 (s, H, =CH-C=O), 6.26 (m, 2H, CH=CH).

EXAMPLE 11

Preparation of 8,14-seco-4,6,9(11)-androstatrien-3,14,17-trione

To a solution of 1-(2-chloroethylidene)-8a-methyl-1,2,6,7,8,8a-hexahydro-6-naphthalenone (1.41 g.) in dimethylformamide (30 ml.) was added sodium iodide (0.940 g.) under nitrogen. The reaction mixture was stirred at room temperature for 10 minutes and the sodium salt of 2-methyl-1,3-cyclopentadione (1.27 g.) dissolved in methanol was added. The reaction mixture was stirred at room temperature for 3 hours. The methanol was evaporated and the inorganic salts precipitated by the addition of ether were filtered and washed with ether. The filtrate was evaporated to dryness and the residue chromatographed on silica gel giving 1.11 g. (63%) of the androstatrien-3,14,17-trione, identical with a sample obtained as described above.

I claim:
1. A compound of the formula

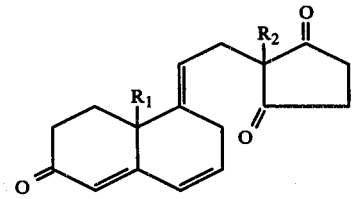

wherein R$_1$ and R$_2$ are each independently lower alkyl and the optical antipodes and geometrical isomers thereof.

2. The compound of claim 1 which is 8,14-seco-4,6,9(11)-androstatriene-3,14,17-trione.